US011559597B2

(12) United States Patent
Sundet et al.

(10) Patent No.: US 11,559,597 B2
(45) Date of Patent: Jan. 24, 2023

(54) MEDICAL DEVICE INSPECTION SYSTEM

(71) Applicant: CLARUS MEDICAL, LLC, Minneapolis, MN (US)

(72) Inventors: Scott Allen Sundet, Edina, MN (US); Cindy Trosen Sundet, Edina, MN (US); Randal Alan Gatzke, Minneapolis, MN (US)

(73) Assignee: Clarus Medical, LLC, Minneapolis, MN (US)

( * ) Notice: Subject to any disclaimer, the term of this patent is extended or adjusted under 35 U.S.C. 154(b) by 958 days.

(21) Appl. No.: 16/253,439

(22) Filed: Jan. 22, 2019

(65) Prior Publication Data
US 2019/0224357 A1    Jul. 25, 2019

Related U.S. Application Data

(60) Provisional application No. 62/620,847, filed on Jan. 23, 2018.

(51) Int. Cl.
*A61L 2/28* (2006.01)
*A61B 90/70* (2016.01)
(Continued)

(52) U.S. Cl.
CPC .............. *A61L 2/28* (2013.01); *A61B 1/0057* (2013.01); *A61B 1/122* (2013.01); *A61B 5/0059* (2013.01);
(Continued)

(58) Field of Classification Search
CPC ..... A61L 2/28; A61L 2/10; A61L 2/24; A61L 2202/11; A61L 2202/14; A61L 2202/24;
(Continued)

(56) References Cited

U.S. PATENT DOCUMENTS 5,626,595 A * 5/1997 Sklar .............. A61B 17/320016
606/180
5,833,683 A   11/1998 Fuller et al.
(Continued)

FOREIGN PATENT DOCUMENTS

JP    H08-24211       1/1996
WO    2017034908 A1   3/2017
(Continued)

OTHER PUBLICATIONS

"Bioprinter with Blue-Light Disinfection Minimizes Need for Cleanrooms," Medical Device and Diagnotic Industry [Online]. Retreived from the Internet: URL: www.mddionline.com/3d-printing/bioprinter-blue-light-disinfection-minimizes-need-cleanrooms, published Dec. 31, 2021, 2 pages.

*Primary Examiner* — David A Vanore
(74) *Attorney, Agent, or Firm* — Merchant & Gould P.C.

(57) ABSTRACT

A medical device inspection system may include a base, a medical device holder on the base, a fiber scope holder on the base, a moveable roller moveably attached to the base such that it is free to rotate around an axis and move from a first position to a second position along the base, and a feeder coupled with the base for feeding a flexible portion of the fiber scope into a lumen of the medical device. During use, the flexible portion of the fiber scope may extend from the handle, around the moveable roller, and through the feeder to enter an opening in the lumen of the medical device.

44 Claims, 6 Drawing Sheets

(51) Int. Cl.
  *A61B 5/00* (2006.01)
  *A61L 2/24* (2006.01)
  *A61L 2/10* (2006.01)
  *A61B 1/005* (2006.01)
  *A61B 1/12* (2006.01)
  *A61M 25/00* (2006.01)
  *A61B 1/00* (2006.01)
  *A61B 90/00* (2016.01)
  *A61B 34/30* (2016.01)

(52) U.S. Cl.
  CPC ............... *A61B 90/70* (2016.02); *A61L 2/10* (2013.01); *A61L 2/24* (2013.01); *A61B 1/00131* (2013.01); *A61B 2034/301* (2016.02); *A61B 2090/066* (2016.02); *A61B 2090/701* (2016.02); *A61B 2090/702* (2016.02); *A61L 2202/11* (2013.01); *A61L 2202/14* (2013.01); *A61L 2202/24* (2013.01); *A61M 2025/0019* (2013.01)

(58) Field of Classification Search
  CPC ..... A61B 1/0057; A61B 1/122; A61B 5/0059; A61B 90/70; A61B 1/00131; A61B 2034/301; A61B 2090/066; A61B 2090/701; A61B 2090/702; A61B 1/00057; A61M 2025/0019; A61M 25/0009
  See application file for complete search history.

(56) References Cited

U.S. PATENT DOCUMENTS

| | | | |
|---|---|---|---|
| 8,593,626 B2 | 11/2013 | Brouwer | |
| 8,933,416 B2 | 1/2015 | Arcand et al. | |
| 9,354,182 B2 | 5/2016 | Rochette et al. | |
| 10,245,339 B2* | 4/2019 | Shin | G02B 23/2476 |
| 10,279,058 B2* | 5/2019 | Lin | A61L 2/10 |
| 10,543,058 B2 | 1/2020 | Bauco et al. | |
| 10,705,020 B2 | 7/2020 | Baribeau | |
| 10,709,313 B2 | 7/2020 | Stephenson | |
| 2009/0099420 A1* | 4/2009 | Woodley | A61B 1/0053 600/142 |
| 2010/0217080 A1 | 8/2010 | Cheung et al. | |
| 2012/0059255 A1* | 3/2012 | Paul | A61B 18/14 600/431 |
| 2012/0071895 A1* | 3/2012 | Stabler | A61B 34/20 606/130 |
| 2015/0012021 A1* | 1/2015 | Mihara | A61B 1/018 606/1 |
| 2015/0182106 A1 | 7/2015 | King | |
| 2015/0231287 A1* | 8/2015 | Lin | A61M 25/0097 607/80 |
| 2019/0038789 A1* | 2/2019 | Kang | A61L 2/16 |
| 2019/0038791 A1 | 2/2019 | Gerrans et al. | |
| 2019/0224357 A1* | 7/2019 | Sundet | A61B 1/0057 |
| 2019/0247050 A1* | 8/2019 | Goldsmith | A61B 17/12181 |
| 2019/0282327 A1 | 9/2019 | Sundet | |
| 2019/0290104 A1* | 9/2019 | Culman | A61B 1/0011 |
| 2019/0357751 A1* | 11/2019 | Friedlander | A61B 1/233 |
| 2021/0213148 A1 | 7/2021 | Gerrans et al. | |
| 2021/0339297 A1 | 11/2021 | Stephenson | |
| 2021/0386443 A1* | 12/2021 | Heimberger | A61B 1/00103 |

FOREIGN PATENT DOCUMENTS

| | | |
|---|---|---|
| WO | WO2020023778 A1 | 1/2020 |
| WO | WO2020096888 A1 | 5/2020 |
| WO | WO2020096889 A1 | 5/2020 |
| WO | WO2020096890 A1 | 5/2020 |
| WO | WO2020096891 A1 | 5/2020 |
| WO | WO2020096892 A1 | 5/2020 |
| WO | WO2020096893 A1 | 5/2020 |
| WO | WO2020096894 A1 | 5/2020 |
| WO | WO2020123679 A1 | 6/2020 |

* cited by examiner

MEDICAL DEVICE INSPECTION SYSTEM

CROSS-REFERENCE TO RELATED APPLICATIONS

This application claims the benefit of U.S. Provisional Patent Application No. 62/620,847, filed Jan. 23, 2018, entitled, "MEDICAL DEVICE INSPECTION SYSTEM." The disclosure of this priority application is hereby incorporated by reference in its entirety into the present application.

TECHNICAL FIELD

This application is directed to medical devices, systems and methods. More specifically, the application is directed to devices, systems and methods for facilitating the inspection of medical devices.

BACKGROUND

Millions of medical devices are used in hospitals throughout the world every day. With the continuing advancement of medical and surgical procedures over time, one of the trends for many years is toward minimally invasive procedures performed through smaller incisions or even through the body's natural orifices. Examples of this trend include arthroscopic surgery, transcatheter aortic valve replacement ("TAVR"), natural orifice transluminal endoscopic surgery ("NOTES"), robotic surgery and many others. Many of these procedures involve the use of long, flexible catheter instruments and/or long, flexible endoscopes for visualizing the procedure. Additionally, endoscopes are used in countless different diagnostic and therapeutic procedures in many parts of the body.

One of the challenges with the use of endoscopes, fiber scopes, catheter-based medical/surgical instruments and other long, thin, reusable instruments is how to properly and effectively clean them. Many endoscopes and other instruments are too expensive to be disposable and so must be reused. And long, small-diameter, flexible instruments can be extremely hard to clean on the inside. They are also hard to inspect on the inside. Not only can flexible instruments collect bacteria and other contaminants, but they can also crack or become otherwise permanently deformed during use, for example when the instrument is bent or kinked. These instruments are typically processed in a cleaning facility located within the hospital, by workers with very little training. To inspect the inside of such instruments, a small, flexible scope is inserted and advanced through the lumen(s) of the device, so that contaminants and damage can be seen. It can be difficult, however, for the person doing the inspection to effectively identify contaminants and internal damage to the device. Thus, the inspection process can be labor intensive and sometimes ineffective.

Therefore, it would be desirable to have improved devices, systems and methods for inspecting medical devices, specifically endoscopes, catheters and other long, thin, flexible medical devices that are difficult to inspect on the inside. At least some of these objectives are addressed in this application.

BRIEF SUMMARY

According to one aspect of the present disclosure, a medical device inspection system includes: a base; a medical device holder on the base, for holding a medical device to be inspected; a fiber scope holder on the base, for holding a handle of a fiber scope; a moveable roller moveably attached to the base such that it is free to rotate around an axis and move from a first position to a second position along the base; and a feeder coupled with the base for feeding a flexible portion of the fiber scope into a lumen of the medical device. During use, the flexible portion of the fiber scope extends from the handle, around the moveable roller, and through the feeder to enter an opening in the lumen of the medical device. The moveable roller is configured to move from the first position that is farthest away from the handle and the feeder to the second position that is closer to the handle and the feeder as the flexible portion is fed into the lumen of the medical device.

In various embodiments, the medical device holder may be a clamp or similar holding device. The feeder may sometimes include a first spinning drum, a drive mechanism attached to the first spinning drum, and a second spinning drum. The flexible portion of the fiber scope may pass between, and be advanced by, the first and second spinning drums. In some embodiments, a contact surface of the first spinning drum and/or a contact surface of the second spinning drum may be made at least partially of a compliant polymer. Some embodiments may also include a tensioner coupled with the feeder to adjust an amount of force applied between the first and second spinning drums.

Some embodiments may also optionally include a controller attached to the feeder, where the controller includes a processor with computer readable instructions for causing the feeder to advance the fiber scope automatically into the lumen of the medical device. In some embodiments, the controller causes the feeder to advance the fiber scope automatically into the lumen in incremental steps. Optionally, the controller may be further in communication with the fiber scope, and the processor may be configured to instruct the fiber scope to capture images at multiple positions within the lumen of the medical device. In some embodiments, the processor is further configured to determine, from an image captured by the fiber scope, that the lumen contains a defect, and instruct the feeder and/or the fiber scope to record a location of the defect in the lumen. For example, the location may be a distance from the opening in the lumen to the defect. In some embodiments, the processor may use artificial intelligence to determine that the lumen contains the defect. For example, the processor may use artificial intelligence to distinguish differently labeled shapes within the lumen of the medical device, such as normal, gouged, oval, wet and debris-containing. In various embodiments, the processor may use artificial intelligence to record an image, a location, a description, a date, a time, a name of a person operating the system, and/or a recommended course of corrective action pertaining to an identified defect in the lumen of the medical device. In some embodiments, artificial intelligence is embodied in an artificial intelligence chip located the base, the feeder, or the fiber scope.

In some embodiments, the handle of the fiber scope and the medical device are attached to the base, such that they face in the same direction, toward the moveable roller. Some embodiments of the system may further include a first fixed roller fixedly attached to the base between the moveable roller and the feeder, where the handle of the fiber scope and the medical device face in different directions. In some embodiments, the system may include a first fixed roller fixedly attached to the base between the moveable roller and the feeder and a second fixed roller fixedly attached to the base between the moveable roller and the fiber scope. In such embodiments, the handle of the fiber scope and the medical device may face toward one another.

In some embodiments, the system may include the fiber scope. For example, the fiber scope may be a water resistant fiber scope. The scope may include multiple internal applications of adhesive to provide water resistance. Optionally, the fiber scope may include an ultraviolet light emitter for emitting light onto a contaminated portion of the lumen of the medical device to help treat the contaminated portion. The fiber scope may further include a light diffuser at or near a distal tip of the fiber scope for diffusing the emitted ultraviolet light. The fiber scope may further include a handle and a flexible portion. The flexible portion may include a sheath, a laser fiber disposed in the sheath to provide kink resistance, at least one light emitting fiber, and at least one image capturing fiber. In alternative embodiments, the fiber scope may include an image capturing chip at a distal end of the sheath. The scope may also include a lock-out feature that prevents use of the fiber scope after a predetermined number of uses. The feeder may include a torque sensor to prevent applying excessive force to the flexible portion of the fiber scope.

In another aspect of the present disclosure, a medical device inspection system may include: a base; a medical device holder on the base, for holding a medical device to be inspected; a roller attached to the base such that it is free to rotate around an axis, wherein the roller holds a flexible portion of a fiber scope; a feeder coupled with the base for feeding the flexible portion of the fiber scope from the roller into a lumen of the medical device; and a communications module for transmitting images captured by the flexible portion of the fiber scope to a handle or other control portion of the fiber scope. During use, the flexible portion of the fiber scope extends from the roller through the feeder to enter an opening in the lumen of the medical device. The communications module may, for example, be a Bluetooth communication module.

In another aspect of the present disclosure, a method for inspecting an inside of a medical device may involve: positioning a flexible fiber scope around a portion of a first roller of a medical device inspection system, such that a handle of the flexible fiber scope is positioned on one side of the first roller and a feeder of the medical device inspection system is on an opposite side of the roller; positioning the flexible fiber scope through the feeder; advancing a distal end of the flexible fiber scope into an opening in a lumen of the medical device; advancing the distal end of the flexible fiber scope farther into the lumen of the medical device, using the feeder, where advancing the distal end farther causes the first roller to turn around an axis and move along the medical device inspection system toward the handle and the feeder; and capturing at least one image of the lumen of the medical device with the flexible fiber scope.

In some embodiments, the method may further involve attaching the medical device to the medical device inspection system before advancing the distal end of the fiber scope into the lumen. In some embodiments, positioning the flexible fiber scope through the feeder may involve positioning the flexible fiber scope between a first spinning drum and a second spinning drum of the feeder. Embodiments may also involve adjusting a tensioner of the medical device inspection system to adjust an amount of force applied to the flexible fiber scope by the first and second spinning drums. In some embodiments, advancing the distal end of the flexible fiber scope farther into the lumen of the medical device is performed automatically by the feeder in a stepwise fashion. Some embodiments may also include recording, with the medical device inspection system, multiple distances into the lumen of the medical device at which images are captured by the flexible fiber scope.

In some embodiments, a controller of the medical device inspection system instructs the flexible fiber scope to acquire at least one image. Optionally, the method may also involve determining, from an image captured by the fiber scope, that the lumen contains a defect, and instructing the feeder and/or the fiber scope to record a location of the defect in the lumen. Some embodiments may further involve determining a distance from the opening in the lumen to a defect in the lumen, using a processor of the medical device inspection system. The method may also involve using artificial intelligence in the medical device inspection system to determine that the lumen contains the defect. Optionally, the method may also involve using the artificial intelligence to distinguish differently labeled shapes within the lumen of the medical device. The method may also involve using the artificial intelligence to record an image, a location, a description, a date, a time, a name of a person operating the system, and/or a recommended course of corrective action pertaining to an identified defect in the lumen of the medical device.

In some embodiments, the method may also involve attaching the handle of the fiber scope to the medical device inspection system. The method may also involve positioning the flexible fiber scope around a first fixed roller fixedly attached to the medical device inspection system between the roller and the feeder. The method may also involve positioning the flexible fiber scope around a second fixed roller fixedly attached to the medical device inspection system between the roller and the handle of the flexible fiber scope. Optionally, the method may involve emitting ultraviolet light from the flexible fiber scope onto a contaminated portion of the lumen of the medical device to help treat the contaminated portion. Such an embodiment may further involve diffusing the ultraviolet light with a light diffuser before emitting it from the flexible fiber scope. In some embodiments, the ultraviolet light may be emitting pulsed light.

In some embodiments, the method may also involve preventing kinking of the flexible fiber scope by housing a laser fiber in a sheath of the flexible fiber scope. In some embodiments, the method may also involve preventing the flexible fiber scope from being used more than a predetermined number of times by including a lock-out feature in the medical device inspection system. The method may further involve preventing the flexible fiber scope from being used with unapproved medical devices or by unapproved inspection personnel by including a lock-out feature in the medical device inspection system. The method may also involve sensing an amount of torque applied to the flexible fiber scope by the medical device inspection system to prevent applying excessive force to the flexible fiber scope.

These and other aspects and embodiments are described more fully below, in reference to the attached drawing figures.

DETAILED DESCRIPTION OF THE INVENTION

Disclosed in this application are various examples of a medical device inspection system and method. In general, the system and method provide for automatic feeding of a fiber scope into the lumen of a medical device in order to inspect the medical device. Feeding of the fiber scope may be done in a stepwise fashion, images may be captured at specified intervals, and the locations of the intervals may be recorded. In some embodiments, artificial intelligence may be used to help the operator of the system identify imperfections in the lumen of the medical device, such as contaminations and defects. These concepts and many others are described in greater detail below. The examples described herein are not intended to limit the scope of the invention but are provided for descriptive purposes only.

Figure 1:
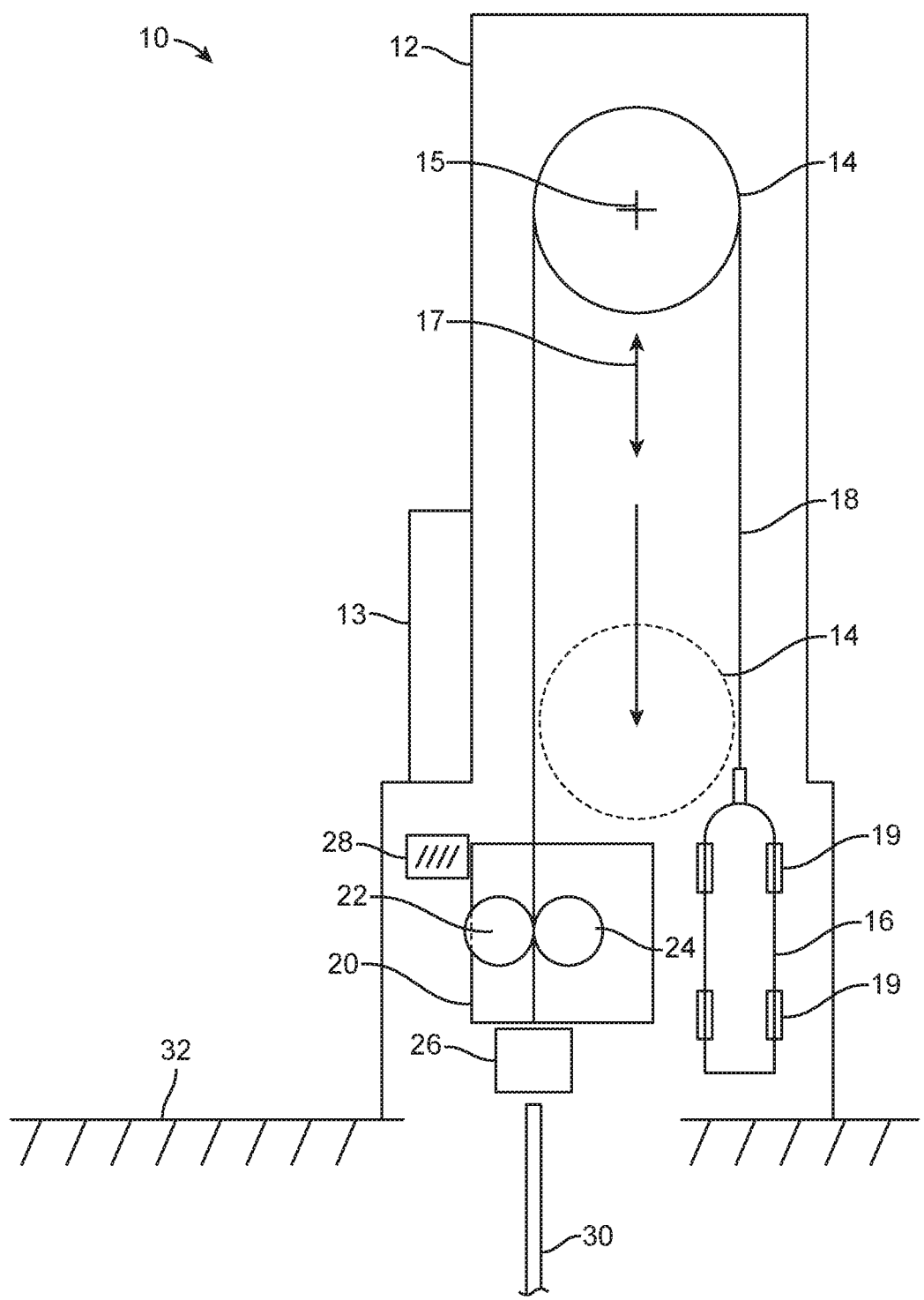
FIG. 1 is a diagrammatic representation of one example of a medical device inspection system.

Referring now to FIG. 1, in one example, a medical device inspection system 10 may include a base 12 (or "tower," in the case of a vertical arrangement, as shown in FIG. 1) and multiple components attached to or embedded in base 12. This embodiment of system 10 is shown with the bottom of base 12 resting on a flat surface 32, such as a table. In another example, system 10 may be flipped, so that base 12 hangs from a ceiling or other elevated structure. In yet another example, base 12 may lie flat on surface 32. Attached to base 12 is a moveable roller 14, which is free to rotate about its central axis of rotation 15 and also move back and forth along a longitudinal axis 17 of base 12. Also attached to base 12 is a fiber scope handle attachment member 19, by which a fiber scope handle 16 is attached to base 12. Handle attachment member 19 may be multiple clips (as shown), clamps or any other suitable attachment structure(s).

Regarding the fiber scope shown in FIG. 1 and subsequent figures, the term "fiber scope" is used in this application to mean any type of elongate, flexible scope device, including a fiber optic scope and/or a digital scope. The fiber scope is shown as including a handle 16, which may include a processor and a light source for the scope, and a flexible, image capturing portion 18, which passes around moveable roller 14 to a feeder 20, which is also attached to base 12. Image capturing portion 18 may include a sheath, one or more fiber optic fibers, a "camera on a chip," such as a CMOS camera and/or the like. In some embodiments (for example, the one shown in FIG. 4), the scope may not include a handle but may house the light source and processor elsewhere.

Feeder 20 includes a first spinning drum 22 and a second spinning drum 24. One of the two drums 22, 24, in this example first drum 22, is connected to a drive mechanism or motor, which spins the first drum 22 about its axis. Second drum 24 spins freely when pressure from first drum 22 is applied to it and motor spins first drum 22. Feeder 20 also includes a tensioner 28 for adjusting an amount of tension between the two surfaces of the two drums 22, 24 against one another. System 10 also includes a medical device attachment clamp 26 (or other attachment member) coupled with base 12, for attaching medical device 30 to system 10. Neither medical device 30 nor surface 32 is typically part of system 10, but they are illustrated for exemplary purposes.

Finally, system 10 may include a display and control module 13 (or multiple modules). Module 13 may include a display portion, such as a video monitor with or without touch screen capabilities. Module 13 may also include one or more controls for controlling feeder 20, controlling the fiber scope and the like. The display portion of module 13 may show images taken with the fiber scope, indicator light(s) signifying a contaminated or damaged area in the lumen of medical device 30, information about a contamination or damaged area in medical device 30, identifying information identifying medical device 30 and/or any other suitable information.

In use, handle 16 is attached to handle attachment member 19, and flexible scope portion 18 is passed around moveable roller and through drums 22, 24. Tensioner 28 is adjusted to adjust the tension placed on flexible portion 18 by drums 22, 24. In one embodiment, the contact (outer) surfaces of drums 22, 24 may be made of nylon or other polymer and may be somewhat compliant, to better advance flexible portion 18 without damaging it. Medical device 30 is attached to clamp 26, and the distal end of flexible portion 18 is advanced into an opening in a lumen at the distal end of medical device 30. Feeder 20 then feeds flexible portion 18 of the fiber scope farther and farther into the lumen of medical device, until the entire device 30 (or a desired portion of device 30) is inspected. As fiber scope 18 advances, it may take multiple still images and/or video images of the lumen. As more and more of fiber scope 18 is advanced into medical device 30, moveable roller 14 moves longitudinally (or "translates") along base 12 from a first position (solid-lined version at the top of FIG. 1) to a second position (dotted-line version at the bottom of FIG. 1), to accommodate for the shorter amount of flexible portion 18 between handle 16 and medical device 30. At the same time, moveable roller 14 also rotates around its rotational axis 15. As illustrated, in the second position, roller 14 is closer to handle 16 and feeder 20 than in the first position. Once flexible portion 18 has been advanced as far into medical device 30 as desired, it is retracted by handle 16, roller 14 and feeder 20, and roller 14 moves back to the first position from the second position.

Control and display module 13 may include any type of computing device, including a processor, and the processor may contain instructions for driving feeder 20 and/or the fiber scope. For example, in some embodiments, the drive mechanism of feeder 20 may be a step motor, and the controller may control incremental advancement of flexible portion 18 into medical device 30 via feeder 20. In some examples, the processor may include an artificial intelligence chip or other mechanism for artificial intelligence. Artificial intelligence may be used, for example, to allow the processor to identify irregularities inside the lumen of medical device 30 in images of the lumen captured by the fiber scope. For example, the processor may be able to identify contaminants, gouges, kinks, cracks, moisture and/or the like inside medical device 30. This identification may be enhanced via artificial intelligence, where the processor has been "taught" to detect irregularities by learning images of similar irregularities in other medical devices. In some embodiments, the processor may be used to detect an irregularity in the lumen during advancement, instruct the fiber scope to capture an image of the irregularity, determine a location of the irregularity in the form of a distance of the irregularity from a distal opening of the lumen, and store identifying information about the type and location of the irregularity in the controller. The controller may also store additional information, such as the type of medical device 30 being examined, the date, the time, the identity of the personnel conducting the examination, how many times the particular fiber scope has been used to inspect medical devices, and/or the like. In some embodiments, feeder 20 feeds flexible portion 18 into medical device 30 in predetermined increments, and an image is taken by the fiber scope at each increment. In other embodiments, the fiber scope may take continual video footage throughout the advancement, and the scope may also take still images at any identified areas of irregularity. Virtually any combination of fiber scope advancement and image capture is possible, and the controller/processor of system 10 may be capable of controlling any of a large number of different protocols.

Additionally, system 10 may be used to inspect any suitable medical or surgical device. The types of devices may include endoscopes of any kind, catheters, flexible instruments with lumens or channels, or virtually any other type of device with an inner portion that is hard to inspect visually from outside the device. System 10 may also have a number of different sizes and shapes in different examples. In the example of FIG. 1, when roller 14 moves all the way to the second position (dotted lines), it may be necessary to have about 12 inches of extra flexible portion 18 of the fiber scope, in order to extend from the distal end of handle 16, around roller 14, through feeder 20 and into the distal end of medical device 30. Other examples of system 10 may require shorter or longer segments of flexible portion.

Figure 2:
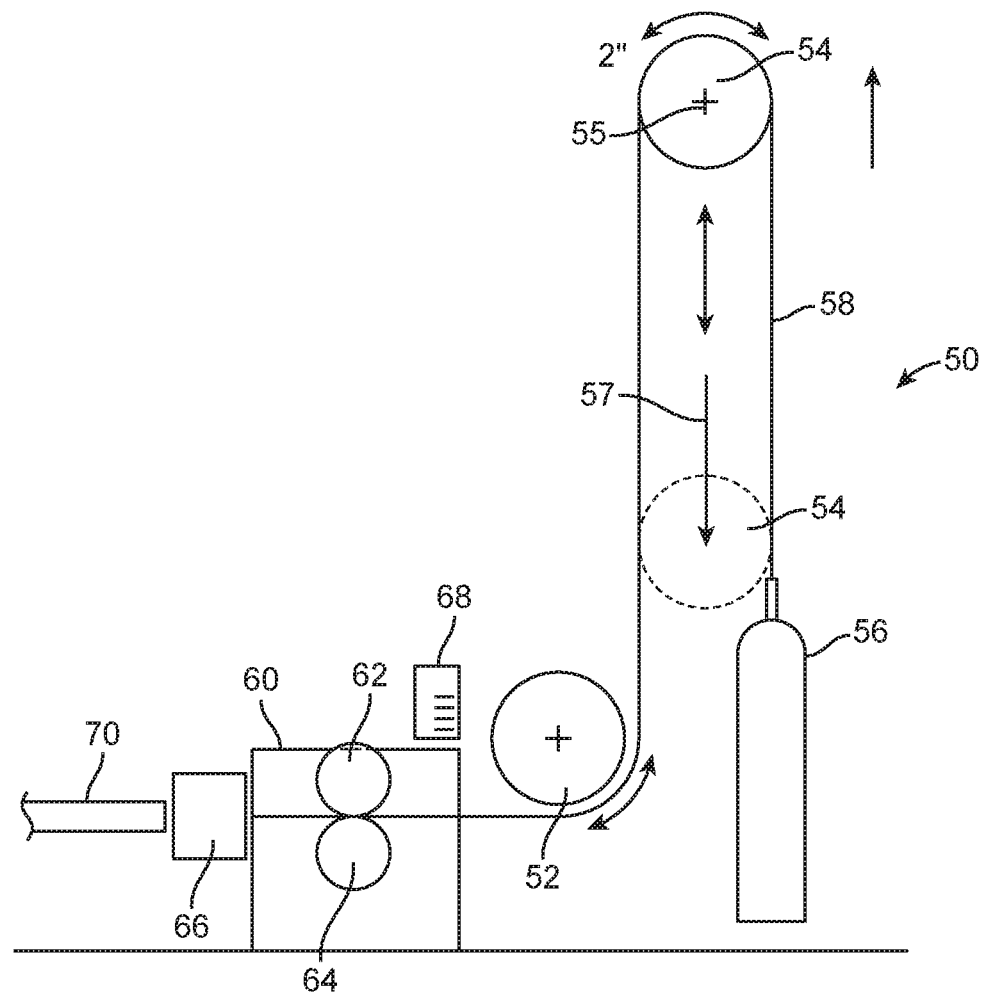
FIG. 2 is a diagrammatic representation of another example of a medical device inspection system.

Referring now to FIG. 2, another example of a medical device inspection system 50 is illustrated diagrammatically. FIG. 2 does not illustrate a base, tower or platform of system 50, and it also does not show the control/display module, but these features may be the same as, or similar to, those shown in FIG. 1, with the exception that the overall system 50 is L-shaped. Similar to the example of FIG. 1, system 50 includes a moveable roller 54, which is rotatable about its own axis 55 and also slidable along a longitudinal axis 57 from a first position to a second position (and back). Roller 54 may be spring loaded (same as in the previous example), so that when it is not under tension it returns to the first position. System 50 also includes a fiber scope with a handle 56 and a flexible portion 58, as well as a feeder 60 with a first spinning drum 62, a second spinning drum 64, a tensioner 68 and a medical device clamp 66, all as described above. A medical device 70 is typically not part of system 50, but rather is the item inspected by system 50.

The main difference between system 50 of FIG. 2 and system 10 of FIG. 1 is that the former includes a second, fixed-location roller 52, about which flexible portion 58 of the fiber scope wraps. This allows the two rollers 52, 54 to act as two pulleys, which may enhance feeding of flexible portion into medical device 70. This example may require a longer extra portion of flexible portion than in the previous example, such as about 14 inches to about 16 inches in one example. In all other respects, system 50 may share any or all of the characteristics and features of system 10 described above.

Figure 3:
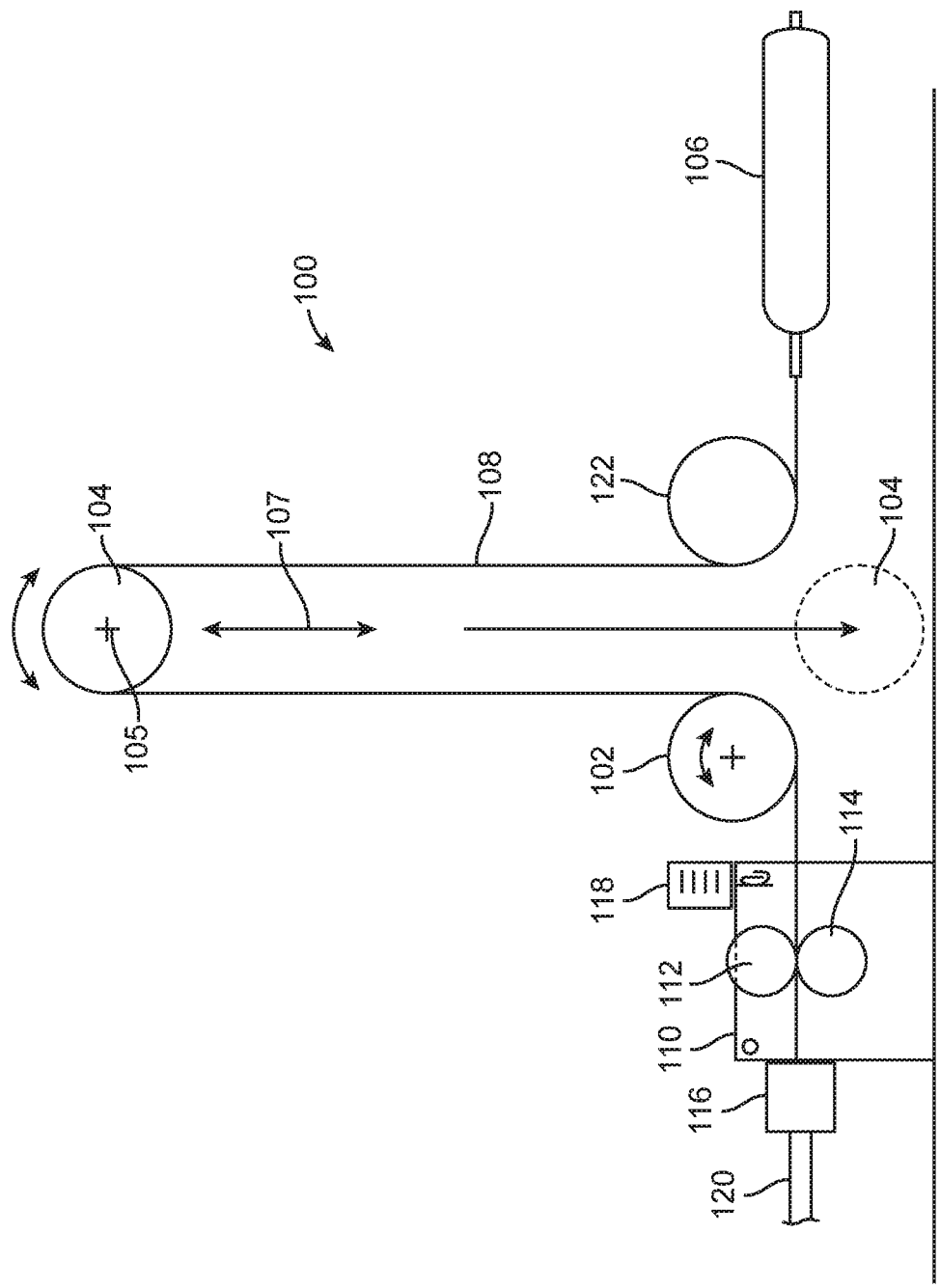
FIG. 3 is a diagrammatic representation of another example of a medical device inspection system.

Referring now to FIG. 3, another example of a medical device inspection system 100 is illustrated diagrammatically. FIG. 3 also does not illustrate a base, platform or tower for holding system 100, but it may be similar to that shown in FIG. 1, with the exception that the overall system 100 has a three-prong (or triangular) shape. Similar to the example of FIG. 2, system 100 includes a moveable roller 104, which is rotatable about its own axis 105 and also slidable along a longitudinal axis 107 from a first position to a second position (and back). Roller 104 may be spring loaded, as described previously. System 100 also includes a fiber scope with a handle 106 and a flexible portion 108, as well as a feeder 110 with a first spinning drum 112, a second spinning drum 114, a tensioner 118 and a medical device clamp 116, all as described above. A medical device 120 is typically not part of system 100, but rather is the item inspected by system 100.

Like system 50 of FIG. 2, system 100 of FIG. 3 includes a second, fixed-location roller 102, about which flexible portion 108 of the fiber scope wraps. Additionally, system 100 includes a fixed cylinder 122, about which flexible portion 108 also wraps. In this example, fixed cylinder 122 does not rotate but merely acts as a third surface about which flexible portion 108 curves, thus providing system 100 with effectively three pulleys. This example may require about 12 inches of extra flexible portion 108 in one example. In all other respects, system 100 may share any or all of the characteristics and features of systems 10 and 50 described above.

Figure 4:
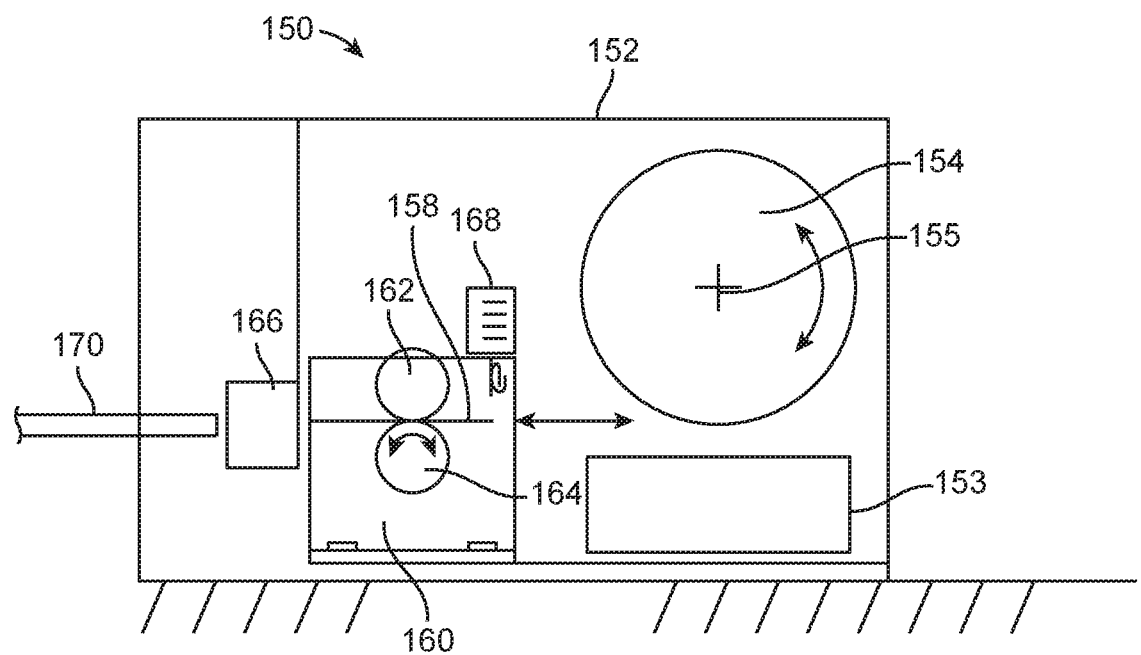
FIG. 4 is a diagrammatic representation of another example of a medical device inspection system.

Referring now to FIG. 4, another example of a medical device inspection system 150 is illustrated diagrammatically. This example of system 150 includes a base 152 and one large roller 154, which rotates about its own axis 155 but is fixed relative to base 152 (e.g., it does not move laterally along base 152). In this embodiment, the fiber scope is housed within roller 154. The processor and light source that are housed in a handle in other embodiments are housed somewhere within roller 154, and the flexible portion 158 is also housed in roller 154 in a spool-like fashion. To advance flexible portion 158 of the fiber scope into medical device 170, roller 154 rotates to unspool flexible portion 158. As in previous embodiments, system 150 also includes a display and control module 153 and a feeder 160 with a first spinning drum 162, a second spinning drum 164, a tensioner 168 and a medical device clamp 166, all as described above. A medical device 170 is typically not part of system 150, but rather is the item inspected by system 150.

The main difference between system 150 of FIG. 4 and previously described embodiments is roller 154, and the housing of the fiber scope in roller 154. In all other respects, system 150 may share any or all of the characteristics and features the previously described embodiments.

Figure 5:
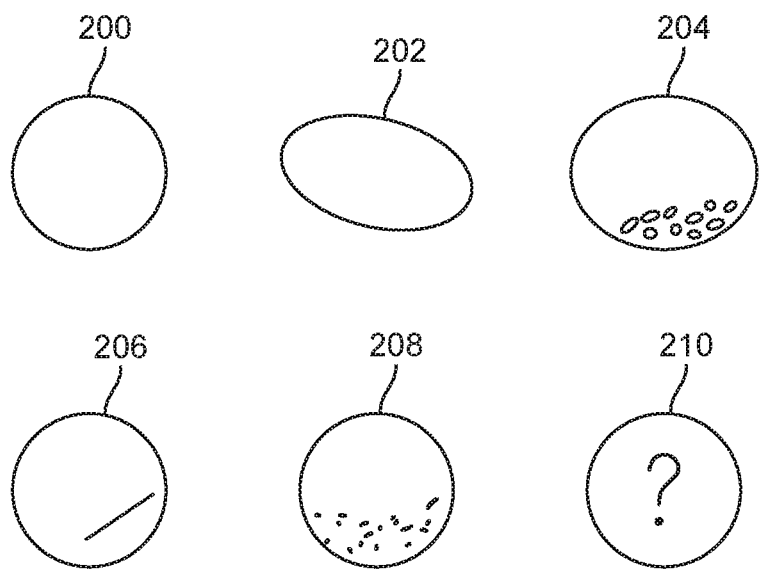
FIG. 5 is a diagrammatic representation of example shapes of an interior of a lumen of a medical endoscope, illustrating a method according to one example.

Referring now to FIG. 5, as mentioned briefly above, in some examples the medical device inspection system may include a computer processor with artificial intelligence capabilities and/or instructions for running an algorithm, either or both of which may allow the system to identify abnormalities within a medical device and even label the abnormalities according to types. For example, the system processor may be able to learn multiple shapes of medical device lumens and identify abnormalities by shape. FIG. 5 illustrates just several examples of such learned shapes. These examples include normal 200, kinked 202 (or oval), wet 204 (signifying accumulated moisture in the device), gouged 206, debris 208 (which could include contamination) and unidentified 210. The last of these—unidentified 210—could be a shape or collection of shapes that the system processor is able to identify as abnormal but is not able to assign to a particular category.

In various examples, the system may do any or all of the following. (1) The feeder may advance the camera through the medical device lumen in stepwise fashion or continuously until the system identifies an abnormality in the lumen, at which point the system may automatically stop advancing the camera and capture a video or still image of the area with the abnormality. (2) The system may identify the abnormality in the lumen based on learned shapes of images of medical device lumens stored in the system's processor. (3)

The system may display the irregularity on the system display with some kind of label, such as a word description and/or an indicator light. (4) The system may provide other information about the irregularity, such as its location in the lumen (a distance from one end of the medical device, for example). (5) The system may automatically emit a UV light to disinfect an identified contamination in the lumen. Any combination of these activities, as well as others, may be performed by the system.

Figure 6:
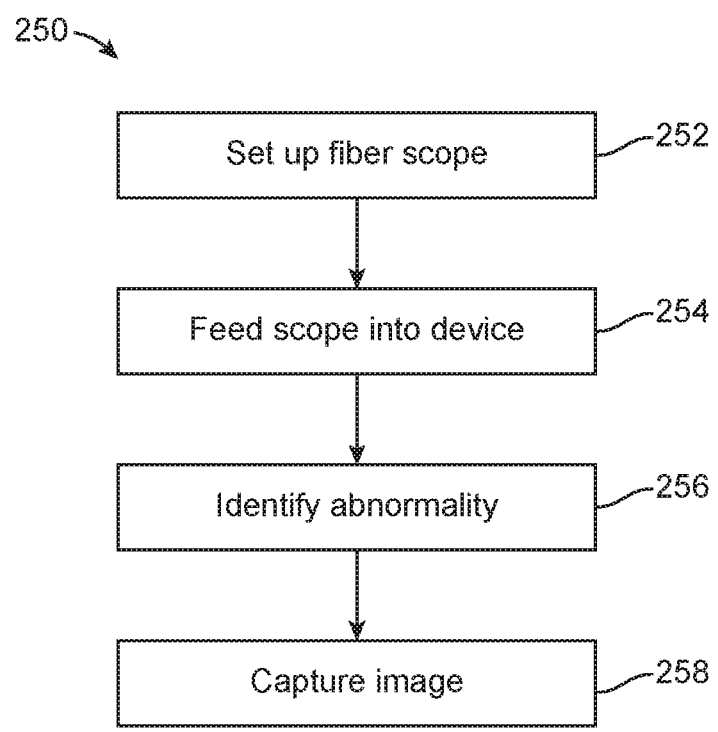
FIG. 6 is a flow diagram of a method of inspecting a medical device, according to one example.

Referring now to FIG. 6, one example of a method 250 for inspecting a medical device, such as a lumen (or "channel") of an endoscope is described. According to one example, a method 250 for inspecting an inside of a medical device may first involve setting up 252 or positioning the fiber scope on or in the medical device inspection system. This step of setting up 252 may include, for example, positioning a flexible fiber scope around a portion of a first roller of a medical device inspection system, such that a handle of the flexible fiber scope is positioned on one side of the first roller and a feeder of the medical device inspection system is on an opposite side of the roller. The method 250 may then involve positioning the flexible fiber scope through the feeder and advancing 254 a distal end of the flexible fiber scope into an opening in a lumen of the medical device. Next, the distal end of the flexible fiber scope is advanced farther into the lumen of the medical device, using the feeder. In some embodiments, all advancement 254 of the fiber scope into the medical device is done through the feeder. Alternatively, the initial advancement 254 may be performed manually, and subsequent advancement 254 may be with the feeder. This advancement 254, in some examples, causes the first roller to turn around an axis and move along the medical device inspection system toward the handle and the feeder. In other embodiments, the first roller does not move along the medical device.

The method may further include identifying an abnormality 256 in the medical device lumen. This identification step may be achieved using the processor, and in some cases artificial intelligence, of the system. Finally, the method may include capturing at least one image 258 of the lumen of the medical device with the flexible fiber scope. This image capturing step 258 may be done automatically in some examples, where the processor identifies the abnormality and sends a signal to the camera to capture the image 258.

In some examples, the method also includes attaching the medical device to the medical device inspection system before advancing the distal end of the fiber scope into the lumen. In some embodiments, positioning the flexible fiber scope through the feeder may involve positioning the flexible fiber scope between a first spinning drum and a second spinning drum of the feeder. Some embodiments may further include adjusting a tensioner of the medical device inspection system to adjust an amount of force applied to the flexible fiber scope by the first and second spinning drums. Advancing the distal end of the flexible fiber scope farther into the lumen of the medical device may sometimes be performed automatically by the feeder in a stepwise fashion.

Some examples of the method may include recording, with the medical device inspection system, multiple distances into the lumen of the medical device at which images are captured by the flexible fiber scope. In some examples, a controller (or processor) of the medical device inspection system instructs the flexible fiber scope to acquire at least one image. In some examples, the method may include distinguishing, from an image captured by the fiber scope, that the lumen contains a defect, and instructing the feeder and/or the fiber scope to record a location of the defect in the lumen. Some examples may involve determining a distance from the opening in the lumen to a defect in the lumen, using a processor of the medical device inspection system.

Some examples of the method involve using artificial intelligence in the medical device inspection system to determine that the lumen contains the defect. Some examples of the method involve using the artificial intelligence to distinguish differently labeled shapes within the lumen of the medical device, where the differently labeled shapes may include normal, gouged, oval, wet and debris-containing. The artificial intelligence may also be used to record an image, a location, a description, a date, a time, a name of a person operating the system, and/or a recommended course of corrective action pertaining to an identified defect in the lumen of the medical device.

In some examples, the method may involve attaching the handle of the fiber scope to the medical device inspection system. Some embodiments may involve positioning the flexible fiber scope around a first fixed roller fixedly attached to the medical device inspection system between the roller and the feeder. Some examples may involve positioning the flexible fiber scope around a second fixed roller fixedly attached to the medical device inspection system between the roller and the handle of the flexible fiber scope.

In some embodiments, the method may involve emitting ultraviolet light from the flexible fiber scope onto a contaminated portion of the lumen of the medical device to help treat the contaminated portion. Alternatively, any other type or wavelength of light may be emitted to treat a contaminated area in a medical device. Light may alternatively or additionally be emitted to help identify an area of damage or contamination in the medical device lumen. For example, chemoluminescence may be used in some examples. In some examples, the method may also include diffusing the ultraviolet light (or other form of light) with a light diffuser before emitting it from the flexible fiber scope. In some embodiments, emitting the ultraviolet light involves emitting pulsed light.

The method may also involve preventing kinking of the flexible fiber scope by housing a laser fiber in a sheath of the flexible fiber scope. The method may also involve preventing the flexible fiber scope from being used more than a predetermined number of times by including a lock-out feature in the medical device inspection system. The method may also involve preventing the flexible fiber scope from being used with unapproved medical devices or by unapproved inspection personnel by including a lock-out feature in the medical device inspection system. The method may also involve sensing an amount of torque applied to the flexible fiber scope by the medical device inspection system to prevent applying excessive force to the flexible fiber scope.

The above description is intended to be complete and accurate. It is meant to be a description of various embodiments, however, and is not intended to limit the scope of the invention. Various changes may be made to any of the embodiments described above, without departing from the scope of the invention described in the following claims. For example, features of one embodiment may be combined with a different embodiment, the order of steps in a given method may be changed, or the like.

We claim:

1. A medical device inspection system, comprising:
a base;
a medical device holder on the base, for holding a medical device to be inspected;

a fiber scope holder on the base, for holding a handle of a fiber scope;
a moveable roller moveably attached to the base such that it is free to rotate around an axis and move from a first position to a second position along the base; and
a feeder coupled with the base for feeding a flexible portion of the fiber scope into a lumen of the medical device,
wherein, during use, the flexible portion of the fiber scope extends from the handle, around the moveable roller, and through the feeder to enter an opening in the lumen of the medical device, and
wherein the moveable roller is configured to move from the first position that is farthest away from the handle and the feeder to the second position that is closer to the handle and the feeder as the flexible portion is fed into the lumen of the medical device.

2. The system of claim 1, wherein the medical device holder comprises a clamp.

3. The system of claim 1, wherein the feeder comprises:
a first spinning drum;
a drive mechanism attached to the first spinning drum; and
a second spinning drum, wherein the flexible portion of the fiber scope passes between and is advanced by the first and second spinning drums.

4. The system of claim 3, wherein a contact surface of the first spinning drum comprises a compliant polymer.

5. The system of claim 4, wherein a contact surface of the second spinning drum comprises the compliant polymer.

6. The system of claim 3, further comprising a tensioner coupled with the feeder to adjust an amount of force applied between the first and second spinning drums.

7. The system of claim 1, further comprising a controller attached to the feeder, wherein the controller comprises a processor with computer readable instructions for causing the feeder to advance the fiber scope automatically into the lumen of the medical device.

8. The system of claim 7, wherein the controller causes the feeder to advance the fiber scope automatically into the lumen in incremental steps.

9. The system of claim 8, wherein the controller is further in communication with the fiber scope, and wherein the processor is further configured to instruct the fiber scope to capture images at multiple positions within the lumen of the medical device.

10. The system of claim 9, wherein the processor is further configured to:
determine, from an image captured by the fiber scope, that the lumen contains a defect; and
instruct at least one of the feeder or the fiber scope to record a location of the defect in the lumen.

11. The system of claim 10, wherein the location comprises a distance from the opening in the lumen to the defect.

12. The system of claim 1, wherein the handle of the fiber scope and the medical device are attached to the base such that they face in the same direction, toward the moveable roller.

13. The system of claim 1, further comprising a first fixed roller fixedly attached to the base between the moveable roller and the feeder, wherein the handle of the fiber scope and the medical device face in different directions.

14. The system of claim 1, further comprising:
a first fixed roller fixedly attached to the base between the moveable roller and the feeder; and
a second fixed roller fixedly attached to the base between the moveable roller and the fiber scope,
wherein the handle of the fiber scope and the medical device face toward one another.

15. The system of claim 1, further comprising the fiber scope.

16. The system of claim 15, wherein the fiber scope is water resistant.

17. The system of claim 16, wherein the fiber scope includes multiple internal applications of adhesive to provide water resistance.

18. The system of claim 15, wherein the fiber scope includes an ultraviolet light emitter for emitting light onto a contaminated portion of the lumen of the medical device to help treat the contaminated portion.

19. The system of claim 18, wherein the fiber scope further includes light diffuser at or near a distal tip of the fiber scope for diffusing the emitted ultraviolet light.

20. The system of claim 15, wherein the fiber scope comprises:
the handle; and
the flexible portion, wherein the flexible portion comprises:
a sheath;
a laser fiber disposed in the sheath to provide kink resistance;
at least one light emitting fiber; and
at least one image capturing fiber.

21. The system of claim 15, wherein the fiber scope comprises:
the handle; and
the flexible portion, wherein the flexible portion comprises:
a sheath;
a laser fiber disposed in the sheath to provide kink resistance;
at least one light emitting fiber; and
an image capturing chip at a distal end of the sheath.

22. The system of claim 15, further including a lock-out feature that prevents use of the fiber scope after a predetermined number of uses.

23. The system of claim 1, wherein the feeder includes a torque sensor to prevent applying excessive force to the flexible portion of the fiber scope.

24. A medical device inspection system, comprising:
a base;
a medical device holder on the base, for holding a medical device to be inspected;
a roller attached to the base such that it is free to rotate around an axis, wherein the roller holds a flexible portion of a fiber scope;
a feeder coupled with the base for feeding the flexible portion of the fiber scope from the roller into a lumen of the medical device; and
a communications module for transmitting images captured by the flexible portion of the fiber scope to a handle or other control portion of the fiber scope,
wherein, during use, the flexible portion of the fiber scope extends from the roller through the feeder to enter an opening in the lumen of the medical device.

25. The system of claim 24, wherein the communications module comprises a wireless communication module.

26. A method for inspecting an inside of a medical device, the method comprising:
positioning a flexible fiber scope around a portion of a first roller of a medical device inspection system, such that a handle of the flexible fiber scope is positioned on one side of the first roller and a feeder of the medical device inspection system is on an opposite side of the roller;

positioning the flexible fiber scope through the feeder;

advancing a distal end of the flexible fiber scope into an opening in a lumen of the medical device;

advancing the distal end of the flexible fiber scope farther into the lumen of the medical device, using the feeder, wherein advancing the distal end farther causes the first roller to turn around an axis and move along the medical device inspection system toward the handle and the feeder; and capturing at least one image of the lumen of the medical device with the flexible fiber scope.

27. The method of claim 26, further comprising attaching the medical device to the medical device inspection system before advancing the distal end of the fiber scope into the lumen.

28. The method of claim 26, wherein positioning the flexible fiber scope through the feeder comprises positioning the flexible fiber scope between a first spinning drum and a second spinning drum of the feeder.

29. The method of claim 28, further comprising adjusting a tensioner of the medical device inspection system to adjust an amount of force applied to the flexible fiber scope by the first and second spinning drums.

30. The method of claim 26, wherein advancing the distal end of the flexible fiber scope farther into the lumen of the medical device is performed automatically by the feeder in a stepwise fashion.

31. The method of claim 30, further comprising recording, with the medical device inspection system, multiple distances into the lumen of the medical device at which images are captured by the flexible fiber scope.

32. The method of claim 26, wherein a controller of the medical device inspection system instructs the flexible fiber scope to acquire at least one image.

33. The method of claim 26, further comprising:

determining, from an image captured by the fiber scope, that the lumen contains a defect; and instructing at least one of the feeder or the fiber scope to record a location of the defect in the lumen.

34. The method of claim 26, further comprising determining a distance from the opening in the lumen to a defect in the lumen, using a processor of the medical device inspection system.

35. The method of claim 26, further comprising attaching the handle of the fiber scope to the medical device inspection system.

36. The method of claim 26, further comprising positioning the flexible fiber scope around a first fixed roller fixedly attached to the medical device inspection system between the roller and the feeder.

37. The method of claim 36, further comprising positioning the flexible fiber scope around a second fixed roller fixedly attached to the medical device inspection system between the roller and the handle of the flexible fiber scope.

38. The method of claim 26, further including emitting ultraviolet light from the flexible fiber scope onto a contaminated portion of the lumen of the medical device to help treat the contaminated portion.

39. The method of claim 38, further comprising diffusing the ultraviolet light with a light diffuser before emitting it from the flexible fiber scope.

40. The method of claim 38, wherein emitting the ultraviolet light comprises emitting pulsed light.

41. The method of claim 26, further comprising preventing kinking of the flexible fiber scope by housing a laser fiber in a sheath of the flexible fiber scope.

42. The method of claim 26, further comprising preventing the flexible fiber scope from being used more than a predetermined number of times by including a lock-out feature in the medical device inspection system.

43. The method of claim 26, further comprising preventing the flexible fiber scope from being used with unapproved medical devices or by unapproved inspection personnel by including a lock-out feature in the medical device inspection system.

44. The method of claim 26, further comprising sensing an amount of torque applied to the flexible fiber scope by the medical device inspection system to prevent applying excessive force to the flexible fiber scope.

* * * * *